US006493888B1

(12) United States Patent
Salvatini et al.

(10) Patent No.: US 6,493,888 B1
(45) Date of Patent: Dec. 17, 2002

(54) PEDIATRIC MATTRESS

(75) Inventors: Benjamin Salvatini, Summerville, SC (US); Kenneth Ray Smith, Charleston, SC (US); John A. Brenner, Goose Creek, SC (US); Kerry Jean Mensching, Mt. Pleasant, SC (US)

(73) Assignee: Hill-Rom Services, Inc., Wilminton, DE (US)

( * ) Notice: Subject to any disclaimer, the term of this patent is extended or adjusted under 35 U.S.C. 154(b) by 0 days.

(21) Appl. No.: 09/551,266

(22) Filed: Apr. 18, 2000

(51) Int. Cl.[7] ........................ A47C 21/04; A47C 27/08; A61G 7/043; A61M 21/00

(52) U.S. Cl. ........................ 5/423; 5/706; 5/715; 5/904

(58) Field of Search ............................ 5/421, 423, 706, 5/710, 713, 714, 715, 724, 726, 652.1, 652.2, 655, 655.3, 659, 660, 904, 914, 941, 945

(56) References Cited

U.S. PATENT DOCUMENTS

| | | | | | |
|---|---|---|---|---|---|
| 1,772,310 | A | * | 8/1930 | Hart | 5/715 X |
| 3,477,071 | A | * | 11/1969 | Emerson | 5/715 X |
| 3,485,240 | A | * | 12/1969 | Fountain | 601/148 |
| 3,513,489 | A | * | 5/1970 | Miller et al. | 5/945 X |
| 3,717,885 | A | * | 2/1973 | De Mare | 5/660 X |
| 3,775,781 | A | * | 12/1973 | Bruno et al. | 5/715 X |
| 4,066,072 | A | * | 1/1978 | Cummins | 5/904 X |
| 4,151,618 | A | * | 5/1979 | Carpenter | 5/284 |
| 4,267,611 | A | * | 5/1981 | Agulnick | 5/713 |
| 4,697,290 | A | * | 10/1987 | Alklind et al. | 5/632 |
| 4,730,604 | A | * | 3/1988 | Boggs | 601/55 |
| 4,905,332 | A | * | 3/1990 | Wang | 5/710 X |
| 4,934,002 | A | * | 6/1990 | Watanabe | 5/715 X |
| 4,947,500 | A | * | 8/1990 | Seiler | 5/706 X |
| 4,977,629 | A | * | 12/1990 | Jones | 5/715 X |
| 5,027,454 | A | * | 7/1991 | Peng | 5/706 X |
| 5,063,912 | A | * | 11/1991 | Hughes | 5/904 X |
| 5,081,722 | A | * | 1/1992 | Yu | 5/423 X |
| 5,092,007 | A | * | 3/1992 | Hasty | 5/715 |
| 5,142,720 | A | * | 9/1992 | Kelso et al. | 5/715 X |
| 5,216,769 | A | * | 6/1993 | Eakin | 5/904 X |
| 5,301,457 | A | * | 4/1994 | Seely | 5/423 X |
| 5,305,483 | A | * | 4/1994 | Watkins | 5/638 |
| 5,313,679 | A | * | 5/1994 | Yamaguchi | 5/659 |
| 5,317,767 | A | * | 6/1994 | Hargest et al. | 5/423 X |
| 5,483,711 | A | * | 1/1996 | Hargest et al. | 5/725 |
| 5,675,852 | A | * | 10/1997 | Watkins | 5/726 X |
| 5,699,569 | A | * | 12/1997 | Schwarz-Zohrer | 5/655 |
| 5,787,534 | A | * | 8/1998 | Hargest et al. | 5/423 X |
| 5,794,289 | A | * | 8/1998 | Wortman et al. | 5/713 |
| 5,865,771 | A | * | 2/1999 | Shuto et al. | 5/904 X |
| 5,887,304 | A | * | 3/1999 | von der Heyde | 5/423 X |
| 5,926,883 | A | * | 7/1999 | Rechin et al. | 5/706 |
| 6,052,853 | A | * | 4/2000 | Schmid | 5/423 X |
| 6,055,690 | A | * | 5/2000 | Koenig | 5/652.1 X |
| 6,131,216 | A | * | 10/2000 | Pine | 5/93.1 |
| 6,145,142 | A | * | 11/2000 | Rechin et al. | 5/706 |
| 6,336,237 | B1 | * | 1/2002 | Schmid | 5/715 |
| 6,370,716 | B1 | * | 4/2002 | Wilkinson | 5/715 |
| 6,370,718 | B1 | * | 4/2002 | Schmid | 5/726 |

FOREIGN PATENT DOCUMENTS

| | | | | | |
|---|---|---|---|---|---|
| DE | 3612362 | A1 | * | 10/1987 | 5/423 |
| EP | 0 491 145 | A1 | * | 10/1991 | |
| EP | 0 986 979 | A1 | * | 9/1999 | |
| FR | 2 641 455 | | * | 12/1988 | |
| GB | 1386249 | | * | 3/1975 | 5/423 |
| WO | WO 86/02815 | | * | 5/1986 | |
| WO | WO-87004934 | | * | 8/1987 | 5/904 |
| WO | WO 98/20828 | | * | 5/1998 | |

* cited by examiner

*Primary Examiner*—Robert G. Santos
(74) *Attorney, Agent, or Firm*—Bose McKinney & Evans LLP

(57) ABSTRACT

A pediatric mattress that includes a sleep surface and a perimeter. The perimeter includes a cavity that is configured to receive the sleep surface. The perimeter also has at least one opening disposed into a chamber positioned within same. The opening is configured such that a gas may flow from the chamber through the opening and over the sleep surface. In addition, the pediatric mattress may include a percussion therapy system. The percussion therapy system includes an audio generator and at least one speaker. The speaker is connected to the audio-signal generator and is configured to produce and direct audio signals to the sleep surface.

25 Claims, 5 Drawing Sheets

PEDIATRIC MATTRESS

BACKGROUND AND SUMMARY OF THE INVENTION

The present invention relates to a mattress. More particularly, the present invention relates to a pediatric mattress.

Ventilated mattresses and percussion therapy are known in the art. Ventilating beds typically consist of a multi-chambered inflatable mattress that vents air through holes provided on its top surface. These holes allow air to escape while an air source continually supplies and maintains the desired amount of inflation to the mattress. This escaping air creates an environment that keeps a patient's skin cool, dry and comfortable.

The present invention provides percussion/audio therapy to a patient in combination with an inflatable air mattress. In addition, the present invention provides a bed that directs a gas and/or audio frequencies to the patient from a variety of directions.

According to the present invention, a mattress includes a sleep surface and a perimeter having a cavity configured to receive the sleep surface and at least one gas outlet located adjacent the cavity. The gas outlet is configured to be coupled to a gas supply to direct gas flow from the gas outlet over the sleep surface.

In the illustrated embodiment, the perimeter includes an inner wall defining the cavity. The perimeter is formed to include an internal chamber having at least one opening extending between the chamber and the inner wall to define the at least one gas outlet. The chamber is configured to be coupled to the gas supply so that the gas is directed through the chamber and the at least one opening and over the sleep surface. Illustratively, the sleep surface is configured to be coupled to the inner wall of the perimeter at a location below the at least one opening.

Also in the illustrated embodiment, a spacer is located within the cavity. The spacer is configured to define first and second bladder cavities. First and second bladders are located in the first and second bladder cavities, respectively, for supporting the sleep surface. The first and second bladders are configured to be selectively inflated and deflated to provide rotational therapy to a patient on the sleep surface.

Also according to the present invention, a mattress includes a sleep surface, a perimeter having a cavity configured to receive the sleep surface, and at least one speaker positioned adjacent the sleep surface. The speaker is configured to direct a desired therapy wave signal to the sleep surface. In the illustrated embodiment, the mattress also includes an audio signal generator coupled to the at least one speaker to supply percussion/vibration therapy to a patient or to play music to be heard by the patient on the sleep surface.

Additional features of the invention will become apparent to those skilled in the art upon consideration of the following detailed description exemplifying the best mode of carrying out the invention as presently perceived.

BRIEF DESCRIPTION OF THE DRAWINGS

The present invention will be described with reference to the attached drawings which are given as non-limiting examples only, in which.

Corresponding reference characters indicate corresponding parts throughout the several views. The drawings set out herein are illustrative embodiments of the invention, and such embodiments are not to be construed as limiting the scope of the invention.

DETAILED DESCRIPTION OF THE DRAWINGS

The present invention relates to a mattress. More particularly, the present invention relates to a pediatric air mattress. The pediatric mattress is of any conventional size to fit on a variety of cribs and/or child beds. In one embodiment, the mattress is configured to provide a cross air flow over a sleep surface of the mattress. In addition, the sleep surface itself is a low-air-loss surface providing air flow directed from the surface to the patient. It is appreciated that the mattress herein described, may be used for any variety of applications beyond just as a pediatric mattress. A low-air-loss mattress allows air to escape from its surface underneath the patient. This creates a drier environment under the patient helping to prevent maceration which is one causative factor in pressure ulcer development. In one embodiment of the present invention, the mattress is configured to include a percussion therapy system to assist in pulmonary cleansing and comfort. The audio or sound resulting from the percussion therapy system is directed through the sleep surface to the patient. Alternatively, the sound is directed into the cross air flow and over the sleep surface to the patient. In this embodiment, the percussion therapy system is integrated into the mattress.

Figure 1:
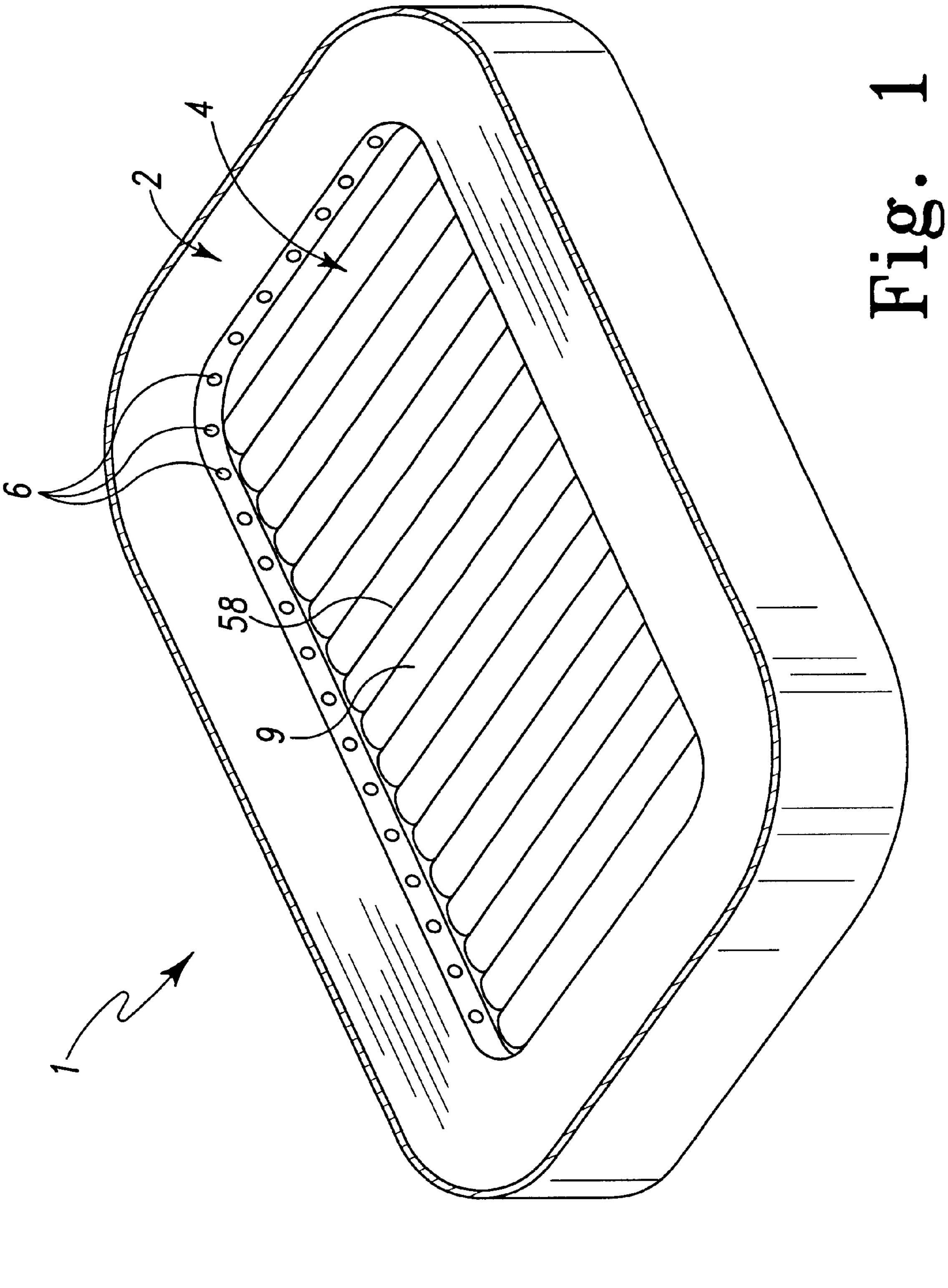
FIG. 1 is a perspective view of a pediatric mattress according to one embodiment of the present invention.

A pediatric mattress according to one embodiment of the present invention is shown in FIG. 1. Mattress 1 comprises a perimeter body 2 forming the border structure of mattress 1. A sleep surface 4 is fitted within perimeter 2. Sleep surface 4 is illustratively an inflatable bed and the portion of mattress 1 that supports a patient 5. (See FIG. 3.) In the illustrated embodiment, a plurality of air holes 6 are positioned in perimeter 2 above sleep surface 4. Holes 6 are configured to direct air flow and/or audio frequencies over sleep surface 4 to patient 5. It is appreciated that any number of holes can be used to create the air flow or the cross air flow. The cross air flow direction is indicated by reference number 32 in FIG. 3.

Figure 2:
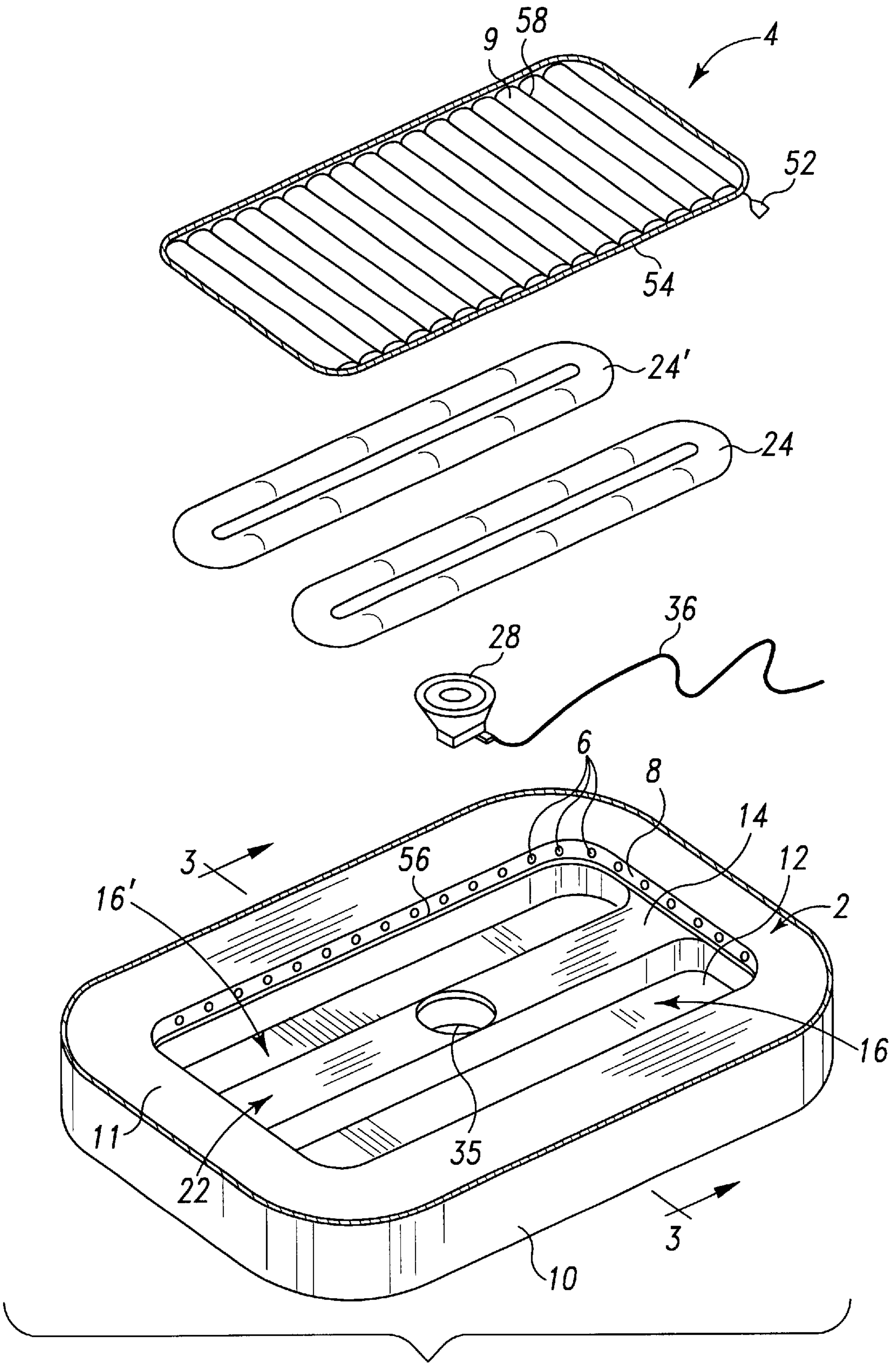
FIG. 2 is an exploded perspective view of the pediatric mattress of FIG. 1.
Figure 3:
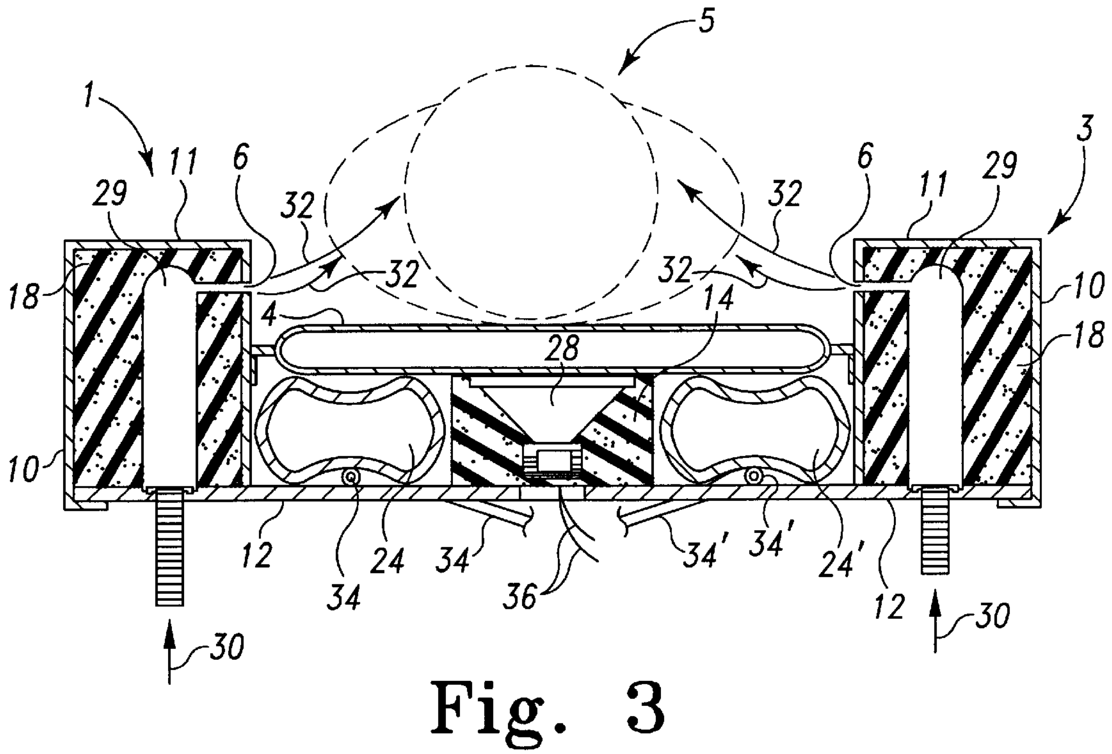
FIG. 3 is a cross sectional end view taken along line 3—3 of FIG. 2.

An exploded view of mattress 1 is shown in FIG. 2. In the illustrated embodiment, perimeter 2 comprises an inner periphery wall 8, an outer periphery wall 10, a deck 11, a base 12, a spacer 14, and bladder cavities 16 and 16'. Inner periphery wall 8 extends upwardly from base 12 and is generally complimentary to the outer shape of sleep surface 4. Outer periphery wall 10 forms the outer boundary of perimeter 2 and is illustratively sized and configured to fit any conventional crib or support. Deck 11 is a top surface extending between the inner and outer periphery walls 8 and 10. A core 18 illustratively provides the body of perimeter 2, as shown in FIG. 3. Core 18 is made from a suitable material such as foam, rubber or other material. It is appreciated, however, that core 18 may be replaced by an inflatable body if desired.

Core 18 is positioned on base 12 that supports pediatric mattress 1. Base 12 spans the area of mattress 1 and is made of any suitable material such as metal, wood, or plastic. Perimeter 2 forms a sleep surface cavity 22. In the illustrative embodiment spacer 14 is positioned within cavity 22 and extends lengthwise therein. Spacer 14 serves several purposes including adding structural support to perimeter 2, separating bladders 24 and 24' and serving as a receptacle for speaker 28 from the percussion therapy system discussed in further detail herein. The spacer 14 is illustratively made from the same materials as core 18. In the illustrated embodiment, spacer 14 separates cavity 22 into first and second bladder cavities 16 and 16'. Bladder cavities 16 and 16' are configured to receive first and second bladders 24 and 24', respectively, as best shown in FIG. 3.

Cross air flow is created by passing air over sleep surface 4. To accomplish this, holes 6 are disposed through inner periphery wall 8. Each hole 6 extends through core 18 into air chamber 29, as best shown in FIG. 3. In one embodiment air chamber 29 is provided within the entire perimeter body 2. (See FIG. 3) Supply tube 30, supplies air from an air source to chamber 29 which is then expelled through air holes 6 as indicated by air directional flow arrows 32. Illustratively, multiple air tubes 30 may be used and be transversely positioned to create an even cross flow of air over sleep surface 4.

In the illustrated embodiment, spacer 14 partitions cavity 22 into first and second bladder cavities 16 and 16' as previously discussed. First and second inflatable bladders 24 and 24' are configured to be received in cavities 16 and 16', respectively, and support sleep surface 4. Illustratively, bladders 24 and 24' are filled with a gas to provide the necessary support. Supply tubes 34 and 34' deliver air to bladders 24 and 24', respectively, to either fill, maintain, or change the level of support. It will be appreciated that any number of bladders may be used to support sleep surface 4. This includes providing one or more bladders that fill the entire area of sleep cavity 20. It is also appreciated that bladders 24 and 24' may be filled with substances other than air. Bladders 24 and 24' may be filled with a foam, gel, or even particulates. Bladders 24 and 24' are illustratively configured to be held loosely in cavities 16 and 16', respectively. In another embodiment, the bladders 24 and 24' are fastened into cavities 16 and 16' by any conventional means including velcro, zippers or an adhesive.

In the illustrated embodiment, a speaker receptacle 35 is formed at a central location along spacer 14. Receptacle 35 is configured to receive and position a speaker 28 so that the speaker 28 directs audio to patient 5. (see FIG. 3.) It will be appreciated that speaker 28 may be a plurality of speakers positioned anywhere along spacer 14, periphery wall 8, bladder cavity 16 and/or 16'. In addition, the speaker 28 may be positioned and configured such that it directs an audio-frequency through air holes 6 to sleep surface 4. In one illustrative embodiment, speaker 28 is connected to an audio-frequency generator (not shown) via speaker wire 36. Wire 36 is configured to allow the audio-frequency generator be either an integral part of mattress 1 or a separate unit. It is appreciated that the audio-frequency generator may be of any conventional type including, but not limited to, a digital audio signal generator, a compact disc or cassette tape player, or a phonograph.

Sleep surface 4 in the illustrated embodiment is positioned within cavity 20 and placed over top of bladders 24, 24' and spacer 14. As shown in FIG. 3, the weight of patient 5 lying on sleep surface 4 creates a downward force that may compress bladders 24 and 24'. Mattress 1 is configured such that bladders 24 and 24' compress to a point substantially adjacent spacer 14. It is appreciated, however, that sleep surface 4 does not have to be positioned adjacent speaker 28 for same to work properly. In another illustrative embodiment, sleep surface 4 includes a zipper 52 and zipper teeth 54 attached at its outer periphery, with corresponding zipper teeth 56 attached to inner wall 8, as shown in FIG. 2. This arrangement allows sleep surface 4 to be secured to mattress 1, yet be easily removed to allow sleep surface 4 to be replaced or to gain access to bladders 24, 24' and/or speaker 28. It is appreciated that sleep surface 4 may be attached to mattress 1 by any conventional means including, but not limited to, velcro, ties, or an adhesive. The sleep surface 4 itself is illustratively an air filled bladder, a multi-chambered bladder, or a series bladders.

Sleep surface 4 in FIGS. 1, 2, 5 and 6 is shown as multi-chambered bladders having a corrugated design 58. It is appreciated that sleep surface 4 may be of any conventional design. Illustratively, sleep surface 4 is a low-air-loss sleep surface. In this embodiment, a plurality of holes (not shown), illustratively about 30 microns in diameter, are disposed through at least one side of said surface, typically the top surface 9. Air is thus allowed to slowly escape sleep surface 4 creating a zone of moving air about the patient. An inflator (not shown) is coupled to sleep surface 4 to replenish the lost air and to adjust the firmness of the surface. In addition, speaker 28 may be positioned to direct sound through said holes to patient 5 to assist the percussion therapy.

In the illustrated embodiment, air is alternately supplied to and removed bladders 24 and 24' to provide rotational therapy to the patient on the sleep surface 4. Illustratively, sleep surface 4 may be unzipped from the perimeter 2 and disposed of after each use. This eliminates the need to sanitize the sleep surface 4 after each use. Speaker 28 provides percussion/vibration therapy to the patient on the sleep surface 4. In addition, music may be played through the speaker 28. This eliminates the need for separate accessory equipment to provide [or] rhythmic sounds for comfort and stimulation of the patient.

Figure 4:
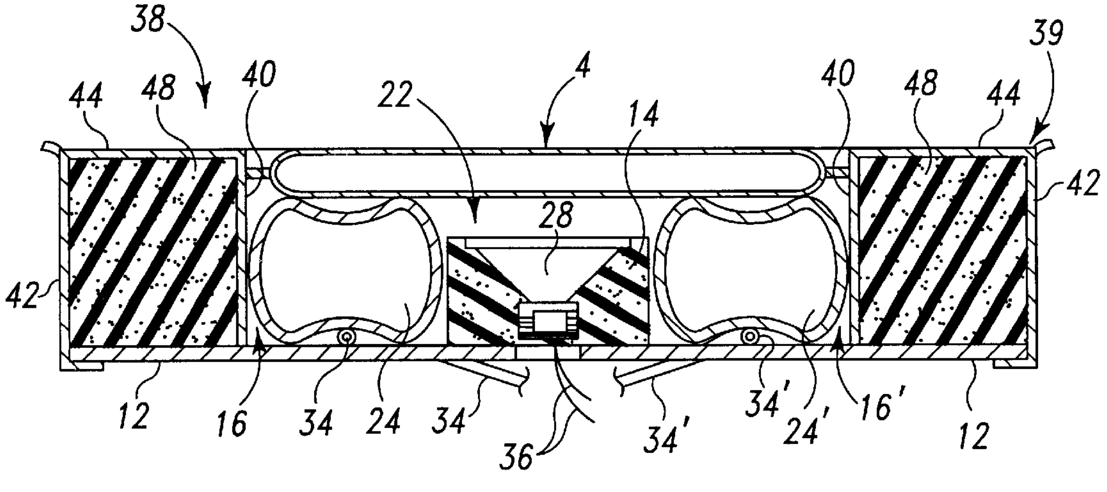
FIG. 4 is a sectional view of another embodiment of the pediatric mattress according to the present invention.

Another embodiment of the present invention is shown in FIG. 4. Pediatric mattress 38, according to this embodiment, comprises a perimeter 39 that forms the outer body of mattress 38. A sleep surface 4 is fitted in perimeter 39. In this illustrated embodiment, perimeter 39 is a border structure comprising an inner periphery wall 40, an outer periphery wall 42, a deck 44, and a base 12, as well as a spacer 14, and bladder cavities 16 and 16' similar to the previous embodiment. This embodiment, however, differs from the previous embodiment in that there are no gas holes disposed through inner periphery wall 40 and no channel provided within core 48. Inner periphery wall 40 extends upwardly from base 12 and is generally the shape of sleep surface 4. Outer periphery wall 42 forms the outer. boundary of perimeter 39 and can be illustratively sized and configured to fit any conventional crib or support, like the previous embodiment. Deck 44 includes an upper surface that is formed parallel to sleep surface 4 and positioned adjacent both inner and outer periphery walls 40 and 42. Inner periphery wall 40, outer periphery wall 42 and deck 44 maintain their shape by being formed over a core 48 that is the shape of perimeter 39. As with core 18, core 48 is made from any suitable material such as foam, rubber or other material.

Core 48 is positioned on base 12 that supports pediatric mattress 38. Illustratively, base 12 spans the area of mattress 38 and is made of any suitable material, such as metal, wood, or plastic. Perimeter 39 forms a sleep surface cavity 22, similar to the previous embodiment. Spacer 14 is illustratively positioned within cavity 22 and extends lengthwise therein. As with the previous embodiment, spacer 14 also serves several purposes, including adding structural support to perimeter 14, separating bladders 24 and 24', and serving as a receptacle for speaker 28 from the percussion therapy system. Like the previous embodiment, it will be appreciated that spacer 14 is illustratively made from the same material as core 18. In the illustrated embodiment, spacer 14 separates cavity 22 into first and second bladder cavities 16 and 16'. Bladder cavities 16 and 16' are configured to receive first and second bladders 24 and 24', as best shown in FIG. 4.

Figure 5:
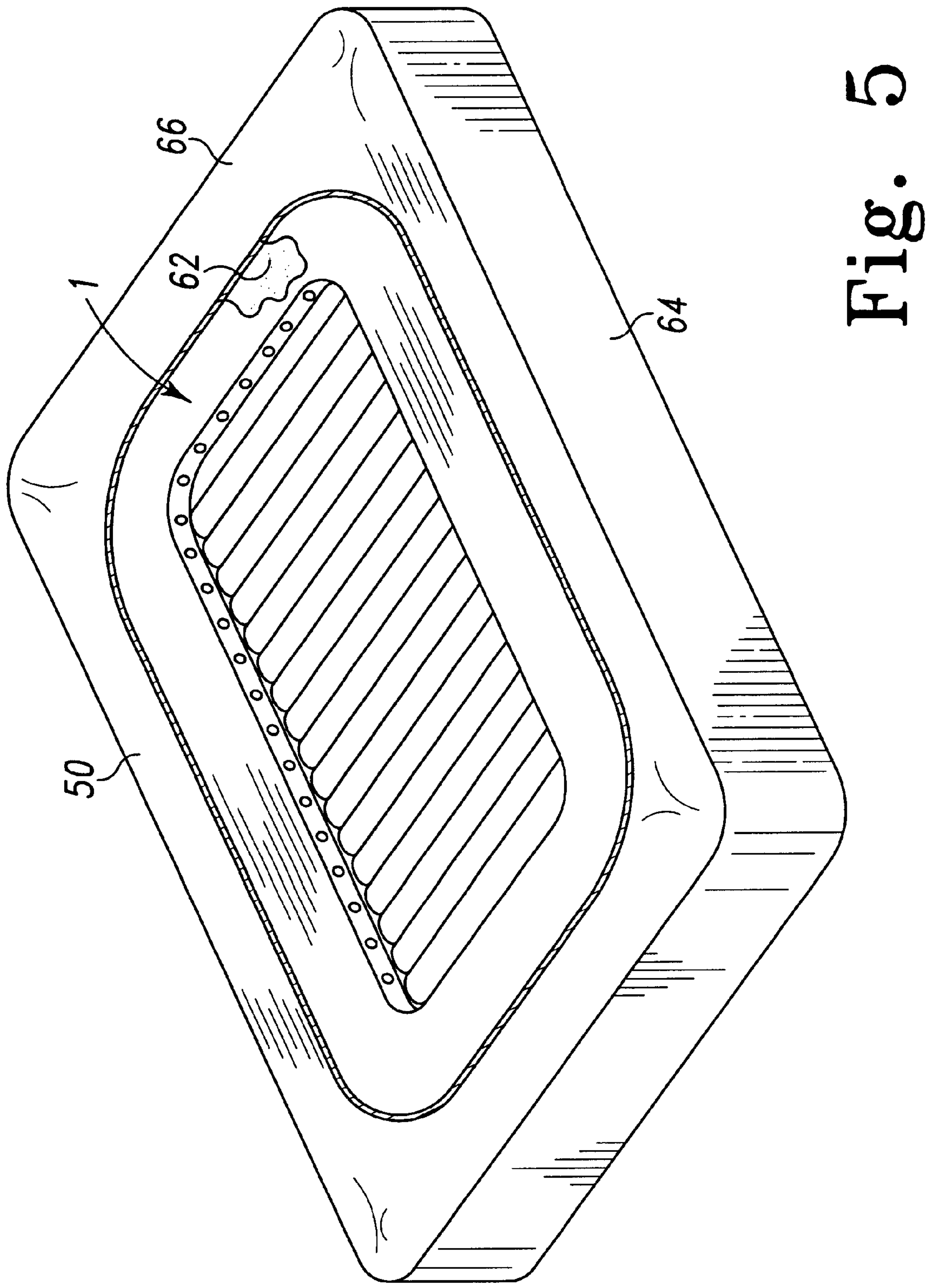
FIG. 5 is a perspective view of the pediatric mattress according to a further embodiment of the present invention.
Figure 6:
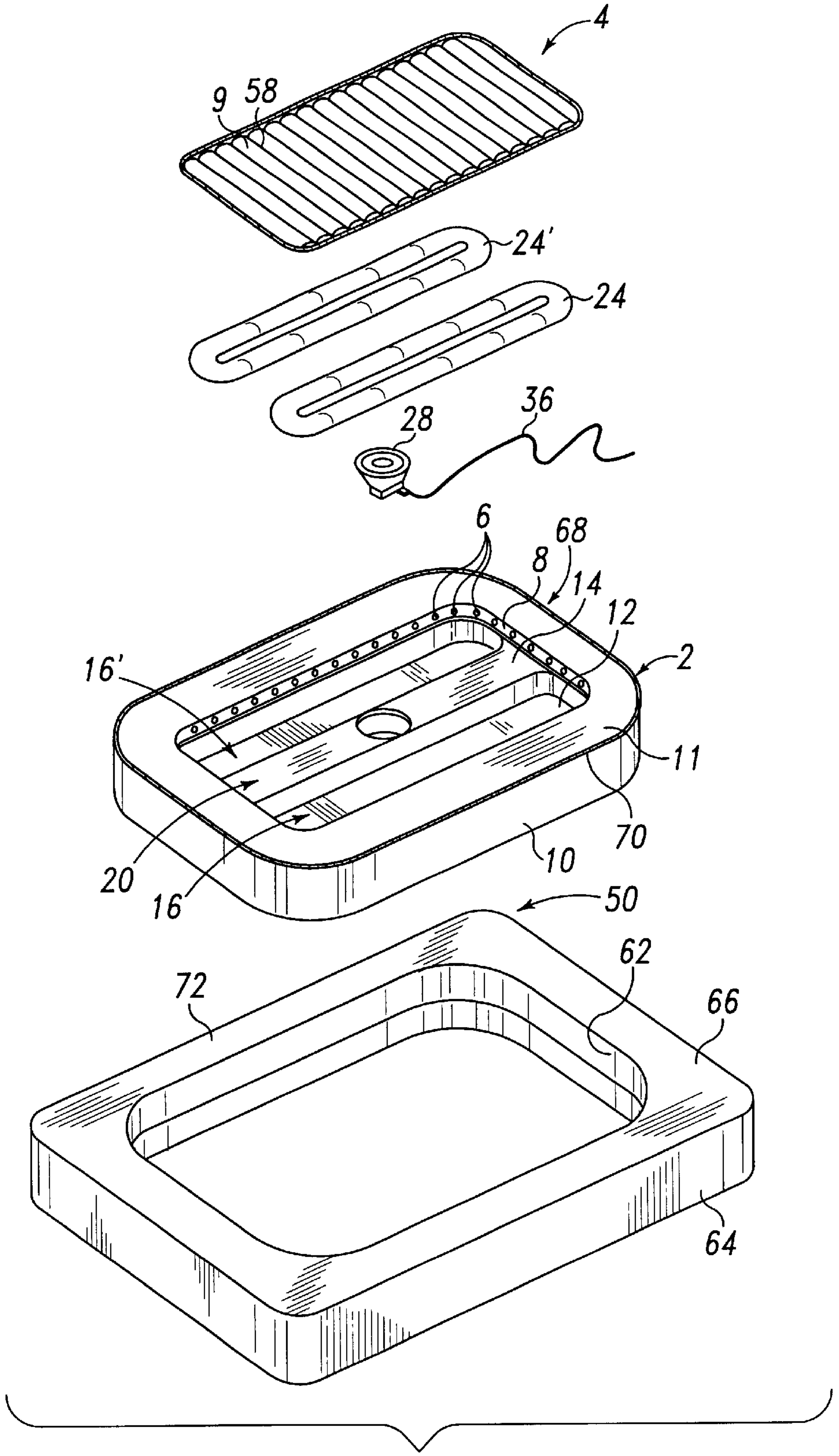
FIG. 6 is an exploded perspective view of the pediatric mattress of FIG. 5.

A further embodiment of the present invention includes a pediatric mattress fitted within a border 50, as shown in FIGS. 5 and 6. Illustratively, either mattress 1 or 38 can be configured to fit within border 50. Border 50 is itself configured to provide additional length and/or width to either mattress 1 or 38 to allow the mattress to be fitted in a larger crib or a larger bed frame. Illustratively, border 50 comprises an inner wall 62, an outer wall 64, and a top surface 66 extending between adjacent inner and outer walls 62 and 64. A core (not shown) provides the body structure for border 50 similar to cores 18 and 46 as shown in FIGS. 3 and 4, respectively. The core of border 50 is illustratively made from the same type of material as cores 18 and 46. In the illustrated embodiment, perimeter 2 includes a zipper 68 and zipper teeth 70 attached at its outer periphery, with corresponding zipper teeth 72 attached to inner wall 66, as shown in FIG. 6. This arrangement allows perimeter 2 to be secured to border 50. It will be appreciated that perimeter 2 may be attached to border 50 by any conventional means including, but not limited to, velcro, ties, or an adhesive. In addition, the border 50 may simply be placed over the perimeter 2 without any fasteners.

Illustratively, perimeter 2 is fitted into border 50 such that deck 11 is positioned in substantially the same plane as top surface 66, as shown in FIG. 5. In the illustrated embodiment, zipper teeth 70 are provided adjacent deck 11 and outer wall 10, and zipper teeth 72 are provided about inner wall 62. The vertically oriented positioning of zipper teeth 72 determines the relative difference in height, if any, between deck 11 and top surface deck 66.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as set forth in the following claims.

What is claimed is:

1. A mattress, comprising:

a sleep surface;

a perimeter having a cavity configured to receive the sleep surface and at least one gas outlet located adjacent the cavity, the gas outlet being configured to be coupled to a gas supply to direct gas flow from the gas outlet over the sleep surface; and at least one bladder positioned within the cavity and configured to support the sleep surface.

2. A mattress, comprising:

a sleep surface;

a perimeter having a cavity configured to receive the sleep surface and at least one gas outlet located adjacent the cavity, the gas outlet being configured to be coupled to a gas supply to direct gas flow from the gas outlet over the sleep surface; and at least two rotational bladders positioned within the cavity and configured to support and provide rotational therapy to the sleep surface.

3. A mattress, comprising:

a sleep surface;

a perimeter having a cavity configured to receive the sleep surface and at least one gas outlet located adjacent the cavity, the gas outlet being configured to be coupled to a gas supply to direct gas flow from the gas outlet over the sleep surface; and a therapy system including an audio generator and at least one speaker positioned within the mattress, the at least one speaker being connected to the audio generator and configured to produce and direct audio signals to the sleep surface;

wherein the at least one speaker is configured to produce audio signals through the gas outlet of the perimeter toward a patient positioned on the sleep surface.

4. A mattress, comprising:

a sleep surface;

a perimeter having a cavity configured to receive the sleep surface and at least one gas outlet located adjacent the cavity, the gas outlet being configured to be coupled to a gas supply to direct gas flow from the gas outlet over the sleep surface; and a spacer located within the cavity, the spacer being configured to define first and second bladder cavities, and first and second bladders located in the first and second bladder cavities, respectively, for supporting the sleep surface.

5. The mattress of claim 4, wherein at least one speaker is located in the spacer.

6. The mattress of claim 4, wherein the first and second bladders are configured to be selectively inflated and deflated to provide rotational therapy to a patient on the sleep surface.

7. A mattress, comprising:

a sleep surface;

a perimeter having an open cavity configured to receive the sleep surface; and at least one speaker substantially enclosed within the cavity below the sleep surface and configured to direct a desired therapy wave signal to the sleep surface.

8. The mattress of claim 7, further comprising an audio signal generator coupled to the at least one speaker.

9. The mattress of claim 7, wherein the perimeter includes an inner wall defining the cavity, the perimeter being formed to include an internal chamber having at least one opening extending between the chamber and the inner wall, the chamber being configured to be coupled to a gas supply so that a gas is directed through the chamber and the at least one opening and over the sleep surface.

10. The mattress of claim 9, wherein the sleep surface is configured to be coupled to the inner wall of the perimeter at a location below the at least one opening.

11. A mattress, comprising:

a sleep surface;

a perimeter having a cavity configured to receive the sleep surface;

at least one speaker positioned adjacent the sleep surface and configured to direct a desired therapy wave signal to the sleep surface;

a spacer located within the cavity, the spacer being configured to define first and second bladder cavities; and first and second bladders located in the first and second bladder cavities, respectively, for supporting the sleep surface.

12. The mattress of claim 11, wherein at least one speaker is located in the spacer.

13. The mattress of claim 11, wherein the first and second bladders are configured to be selectively inflated and deflated to provide rotational therapy to a patient on the sleep surface.

14. A mattress, including:

a sleep surface; and a perimeter having a cavity to receive the sleep surface, the cavity having a lower portion between the sleep surface and a bottom wall of the cavity, a chamber isolated from the cavity lower portion by a wall of the perimeter, and at least one gas outlet located above the sleep surface and coupled to the perimeter chamber to direct gas flow from the chamber over the sleep surface.

15. The mattress of claim 14, wherein the at least one gas outlet includes a plurality of openings formed in the perimeter in communication with a chamber formed in the perimeter, the openings being positioned intermittently about the perimeter and configured to direct gas flow from the plurality of openings over the sleep surface.

16. The mattress of claim 14, further comprising a therapy system including an audio generator and at least one speaker positioned within the mattress, the at least one speaker being connected to the audio generator and configured to produce and direct audio signals to the sleep surface.

17. The mattress of claim 16, wherein the sleep surface is formed to include a plurality of holes disposed through a surface of said sleep surface through which gas passes.

18. The mattress of claim 14, further comprising a border configured to be positioned around the perimeter.

19. The mattress of claim 14, wherein the perimeter includes an inner wall defining the cavity, the perimeter being formed to include an internal chamber having at least one opening extending between the chamber and the inner wall to define the at least one gas outlet, the chamber being configured to be coupled to a gas supply so that the gas is directed through the chamber and the at least one opening and over the sleep surface.

20. The mattress of claim 19, wherein the sleep surface is configured to be coupled to the inner wall of the perimeter at a location below the at least one opening.

21. A mattress, including:

a sleep surface;

a perimeter having a cavity with an inner wall to receive the sleep surface, and at least one gas outlet to direct gas flow toward a person on the sleep surface; and a fastener configured to provide a substantially continuous connection between a periphery of the sleep surface and the cavity inner wall.

22. The mattress of claim 21, wherein the fastener includes a zipper.

23. A mattress, including:

a perimeter forming a cavity having a bottom wall and an inner wall defining an area;

a patient support portion disposed within the cavity and having an impermeable surface substantially spanning the cavity area; and a gas outlet formed in the inner wall of the perimeter to direct gas flow over the patient support portion.

24. The mattress of claim 23, wherein the patient support portion includes a bladder.

25. The mattress of claim 23, wherein the impermeable surface is a bottom surface of the patient support portion.

* * * * *